United States Patent
Gantenbein et al.

(10) Patent No.: US 10,308,518 B2
(45) Date of Patent: Jun. 4, 2019

(54) METHOD FOR THE MANUFACTURING OF A SUSPENSION COMPRISING A CALCIUM CARBONATE-COMPRISING MATERIAL

(71) Applicant: Omya International AG, Oftringen (CH)

(72) Inventors: Daniel Gantenbein, Basel (CH); Espen Berg-Hansen, Molde (NO); Rolf Endre Orten, Molde (NO)

(73) Assignee: Omya International AG, Oftringen (CH)

(*) Notice: Subject to any disclaimer, the term of this patent is extended or adjusted under 35 U.S.C. 154(b) by 0 days.

(21) Appl. No.: 15/518,978

(22) PCT Filed: Oct. 30, 2015

(86) PCT No.: PCT/EP2015/075266
§ 371 (c)(1),
(2) Date: Apr. 13, 2017

(87) PCT Pub. No.: WO2016/071226
PCT Pub. Date: May 12, 2016

(65) Prior Publication Data
US 2017/0240433 A1     Aug. 24, 2017

(30) Foreign Application Priority Data
Nov. 7, 2014 (EP) .................... 14192356

(51) Int. Cl.
*C01F 11/18* (2006.01)
*A61K 8/19* (2006.01)
(Continued)

(52) U.S. Cl.
CPC ........... *C01F 11/185* (2013.01); *A61K 8/19* (2013.01); *A61Q 19/00* (2013.01); *C04B 14/28* (2013.01);
(Continued)

(58) Field of Classification Search
CPC .......... A61K 2800/10; A61K 2800/612; A61K 8/19; A61Q 19/00; C01F 11/185;
(Continued)

(56) References Cited

U.S. PATENT DOCUMENTS

| 5,558,850 A | 9/1996 | Bleakley et al. |
| 5,879,442 A | 3/1999 | Nishiguchi et al. |

(Continued)

FOREIGN PATENT DOCUMENTS

| CN | 101351510 A | 1/2009 |
| EP | 0850880 A1 | 7/1998 |

(Continued)

OTHER PUBLICATIONS

International Search Report dated May 2, 2016 for PCT/EP2015/075266.
Written Opinion of the International Searching Authority dated May 2, 2016 for PCT/EP2015/075266.
Office Action dated Jun. 19, 2018 for Chinese Application No. 201580060627.9.
Search Report dated Jun. 1, 2018 for Chinese Application No. 201580060627.9.
(Continued)

*Primary Examiner* — Shuangyi Abu Ali
(74) *Attorney, Agent, or Firm* — Amster, Rothstein & Ebenstein LLP

(57) ABSTRACT

The present invention relates to a process for the manufacturing of a calcium carbonate-comprising material, to a calcium carbonate-comprising material obtained by the process as well as the use of the calcium carbonate-comprising material for paper filler and paper coating applications, in plastics applications, in paints, in adhesives, in sealings, in concrete, in agriculture applications, in food applications, in cosmetic applications or in pharmaceutical applications.

27 Claims, 1 Drawing Sheet

(51) Int. Cl.
*A61Q 19/00* (2006.01)
*C08K 3/26* (2006.01)
*C09C 1/02* (2006.01)
*C04B 14/28* (2006.01)
*C09C 3/04* (2006.01)
*D21H 17/67* (2006.01)
*D21H 19/38* (2006.01)
*C09D 7/62* (2018.01)
*C08K 9/04* (2006.01)
*C09C 3/08* (2006.01)
*C09J 11/04* (2006.01)

(52) U.S. Cl.
CPC ............... *C08K 3/26* (2013.01); *C08K 9/04* (2013.01); *C09C 1/021* (2013.01); *C09C 3/041* (2013.01); *C09C 3/08* (2013.01); *C09D 7/62* (2018.01); *C09J 11/04* (2013.01); *D21H 17/675* (2013.01); *D21H 19/385* (2013.01); A61K 2800/10 (2013.01); A61K 2800/612 (2013.01); C01P 2004/51 (2013.01); C01P 2004/61 (2013.01); C01P 2004/62 (2013.01); C01P 2006/12 (2013.01); C01P 2006/22 (2013.01); C01P 2006/60 (2013.01); C08K 2003/265 (2013.01); C08K 2201/003 (2013.01); C08K 2201/006 (2013.01)

(58) Field of Classification Search
CPC .............. C01P 2004/61; C01P 2004/62; C01P 2006/12; C01P 2006/22; C04B 14/28; C08K 2003/265; C08K 2201/003; C08K 2201/006; C08K 3/26; C08K 9/04; C09C 1/021; C09C 3/041; C09C 3/08; C09D 7/1225; C09D 7/62; C09J 11/04; D21H 17/675; D21H 19/385
See application file for complete search history.

(56) References Cited

U.S. PATENT DOCUMENTS

| | | |
|---|---|---|
| 2004/0250970 A1 | 12/2004 | Qiu et al. |
| 2008/0308010 A1* | 12/2008 | Rainer .................. C01F 11/185 106/450 |
| 2009/0298988 A1 | 12/2009 | Jacquemet et al. |
| 2010/0035076 A1 | 2/2010 | Kostuch et al. |
| 2012/0302689 A1 | 11/2012 | Jacquemet et al. |
| 2014/0299823 A1 | 10/2014 | Gane et al. |

FOREIGN PATENT DOCUMENTS

| | | |
|---|---|---|
| EP | 1764345 A1 | 3/2007 |
| EP | 2722368 A1 | 4/2014 |
| EP | 2770017 A1 | 8/2014 |
| JP | H10194735 A | 7/1998 |
| JP | 2006505701 A | 2/2006 |
| JP | 2009508792 A | 3/2009 |
| JP | 2009522189 A | 6/2009 |
| JP | 2009531267 A | 9/2009 |
| JP | 2014514393 A | 6/2014 |
| RU | 2451707 C2 | 5/2012 |
| UA | 97094 C2 | 1/2012 |
| UA | 100494 C2 | 1/2013 |
| WO | 2013/120934 A1 | 8/2013 |
| WO | 2014/009396 A2 | 1/2014 |

OTHER PUBLICATIONS

European Search Report and Annex to the European Search Report dated May 15, 2015 for European Application No. EP14192356.5.
Russian Search Report dated Apr. 16, 2018 for Russian Application No. 2017119656.
International Preliminary Report on Patentability dated May 9, 2017 for PCT/EP2015/075266.

* cited by examiner

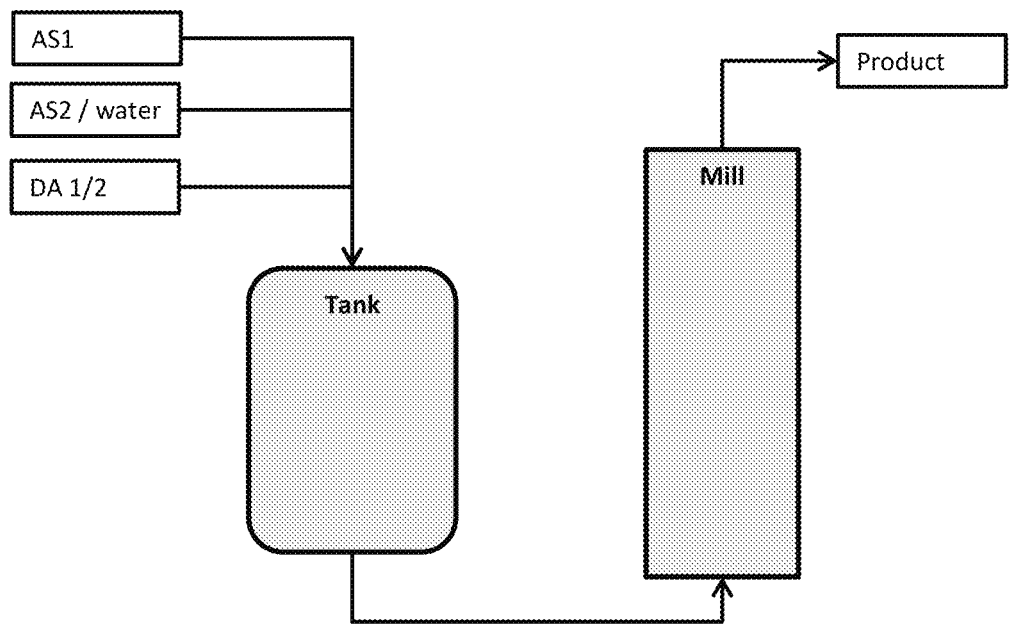

METHOD FOR THE MANUFACTURING OF A SUSPENSION COMPRISING A CALCIUM CARBONATE-COMPRISING MATERIAL

CROSS-REFERENCE TO RELATED APPLICATIONS

This is a U.S. national phase of PCT Application No. PCT/EP2015/075266, filed Oct. 30, 2015, which claims priority to European Application No. 14192356.5, filed Nov. 7, 2014.

The present invention relates to a process for the manufacturing of a calcium carbonate-comprising material, to a calcium carbonate-comprising material obtained by the process as well as the use of the calcium carbonate-comprising material for paper filler and paper coating applications, in plastics applications, in paints, in adhesives, in sealants, in concrete, in agriculture applications, in food applications, in cosmetic applications or in pharmaceutical applications.

In practice, aqueous preparations and especially suspensions of water-insoluble solids such as calcium carbonate-comprising materials are used extensively in agricultural and pharmaceutical applications as well as in the paper, paint, rubber and plastics industries as coatings, fillers, extenders and pigments for papermaking as well as aqueous lacquers and paints. For example, suspensions or slurries of calcium carbonate, talc or kaolin are used in the paper industry in large amounts as filler and/or as a component in the preparation of coated paper. Typical aqueous preparations of water-insoluble solids are characterized in that they comprise water, a water-insoluble solid compound and optionally further additives, such as dispersing agents, in the form of a suspension or slurry.

Thus, there is a great demand for processes for the production of calcium carbonate-comprising materials having specific properties. A great variety of processes has been proposed in this regard. For example, US 2010/0035076 A1 refers to a process for producing a particulate calcium carbonate having a desired particle size distribution, the process comprising: grinding a calcium carbonate feed at a first location to produce a first ground calcium carbonate having a particle size distribution ranging from about 5% less than 2 micrometers to about 75% less than 2 micrometers; stabilizing the first ground calcium carbonate; transporting the stabilized ground calcium carbonate to a second location; and further grinding the stabilized ground calcium carbonate at the second location to produce a particulate calcium carbonate having a desired particle size distribution.

However, the expert is still faced with the problem of efficient manufacturing of calcium carbonate-comprising materials providing low BET specific surface area. A low BET specific surface area of a calcium carbonate-comprising material is desirable as such a material results in a lower consumption of dispersing agents in combination with improved optical properties as well as coating hold out.

Thus, there is still a need in the art to provide calcium carbonate-comprising materials and processes for their manufacturing which provide a better performance than existing calcium carbonate-comprising materials and especially allows for providing a calcium carbonate-comprising material having a low BET specific surface area. In particular, it is desired to provide calcium carbonate-comprising materials having lower BET specific surface area as compared to calcium carbonate-comprising materials manufactured by conventional processes using one aqueous suspension of calcium carbonate-comprising material and optionally water. Thus, it is also desired to provide a calcium carbonate-comprising material that decreases the overall consumption of dispersing agent but improves the optical properties as well as coating hold out. It is further desired to provide a process for the manufacturing of calcium carbonate-comprising materials which is more time efficient and therefore is also more energy efficient compared to conventional processes for the manufacturing of calcium carbonate-comprising materials using one aqueous suspension of calcium carbonate-comprising material and optionally water.

It is thus an object of the present invention to provide a process for the manufacturing of a calcium carbonate-comprising material. Another object may also be seen in the provision of an efficient process for lowering the BET specific surface area of a calcium carbonate-comprising material. A further object of the present invention is to provide a process for the manufacturing of a calcium carbonate-comprising material which provides a material that decreases the overall consumption of dispersing agent but improves the optical properties as well as the coating hold out. A still further object may be seen in the provision of a more time-efficient process for the manufacturing of a calcium carbonate-comprising material.

BRIEF DESCRIPTION OF THE FIGURES

FIG. 1: Block diagram of a process of the invention showing Aqueous Suspension 1, Aqueous Suspension 2 and Dispersing Agent.

DETAILED DESCRIPTION

The foregoing and other objectives are solved by a process for the manufacturing of a calcium carbonate-comprising material, the process comprising the steps of
a) providing at least two aqueous suspensions comprising a calcium carbonate-comprising material, wherein
  i) the first aqueous suspension has a solid content from 1.0 to 82.0 wt.-%, based on the total weight of the aqueous suspension, and a content of particles having a particle size <2 µm in the range from 1.0 to 30.0 wt.-%; and
  ii) the second aqueous suspension has a solid content from 10.0 to 82.0 wt.-%, based on the total weight of the aqueous suspension, and a content of particles having a particle size <2 µm in the range from >30.0 to 100.0 wt.-%;
b) mixing the at least two aqueous suspensions provided in step a) to obtain an aqueous suspension mixture;
c) grinding the aqueous suspension mixture obtained in mixing step b) and/or at least one of the at least two aqueous suspensions provided in step a) before mixing step b) is carried out.

It should be understood that for the purposes of the present invention, the following terms have the following meaning:

The term "calcium carbonate-comprising material" refers to a material comprising at least 50.0 wt.-% calcium carbonate, based on the total dry weight of the calcium carbonate-comprising material.

Unless specified otherwise, the term "drying" refers to a process according to which at least a portion of water is removed from a material to be dried. Moreover, a "dried" material may be further defined by its total moisture content which, unless specified otherwise, is less than 3.0 wt.-%, preferably in the range from 0.05 to 0.2 wt.-%, more preferably in the range from 0.01 to 0.1 wt.-%, based on the total weight of the calcium carbonate-comprising material.

Unless indicated otherwise, the "total moisture content" of a material can be measured according to the Karl Fischer coulometric titration method, desorbing the moisture in an oven at 220° C. for 10 min and passing it continuously into a Karl Fischer coulometer (Mettler-Toledo coulometric KF Titrator C30, oven DO 0337) using dry nitrogen at 100 ml/min for 10 min. In this context, a calibration curve using water should be recorded and a blank of 10 min nitrogen flow without a sample has to be taken into account.

Throughout the present application, the particle size of a calcium carbonate and other materials is described by its distribution of particle sizes. The value $d_x$ represents the diameter relative to which x % by weight of the particles have diameters less than $d_x$. This means that the $d_{20}$ value is the particle size at which 20 wt.-% of all particles are smaller, and the $d_{75}$ value is the particle size at which 75 wt.-% of all particles are smaller. The $d_{50}$ value is thus the weight median particle size at which 50 wt.-% of all grains are bigger and 50 wt.-% are smaller than this particle size. The $d_{98}$ value (also referred to as the "topcut") is the particle size at which 98 wt.-% of all particles are smaller than the indicated value. For the purpose of the present invention the particle size is specified as weight median particle size $d_{50}$ unless indicated otherwise. Unless indicated otherwise, the particle size of a material is measured by using a Sedigraph™ 5120 or a Sedigraph™ 5100 of Micromeritics Instrument Corporation.

Where an indefinite or definite article is used when referring to a singular noun, e.g., "a", "an" or "the", this includes a plural of that noun unless anything else is specifically stated.

Where the term "comprising" is used in the present description and claims, it does not exclude other elements. For the purposes of the present invention, the term "consisting of" is considered to be a preferred embodiment of the term "comprising". If hereinafter a group is defined to comprise at least a certain number of embodiments, this is also to be understood to disclose a group, which preferably consists only of these embodiments.

Terms like "obtainable" or "definable" and "obtained" or "defined" are used interchangeably. This, for example, means that, unless the context clearly dictates otherwise, the term "obtained" does not mean to indicate that, for example, an embodiment must be obtained by, e.g. the sequence of steps following the term "obtained" though such a limited understanding is always included by the terms "obtained" or "defined" as a preferred embodiment.

According to another aspect of the present invention, a calcium carbonate-comprising material obtained by the instant process is provided. According to a further aspect, the use of the calcium carbonate-comprising material for paper filler and paper coating applications, in plastics applications, in paints, in adhesives, in sealants, in concrete, in agriculture applications, in food applications, in cosmetic applications or in pharmaceutical applications is provided.

Advantageous embodiments of the present invention are defined in the corresponding sub-claims.

According to one embodiment of the instant process, at least one dispersing agent is added to at least one of the at least two aqueous suspensions provided in step a) and/or to the aqueous suspension mixture obtained in mixing step b).

According to another embodiment of the instant process, the at least one dispersing agent is selected from the group consisting of sodium, potassium, calcium, magnesium, lithium, strontium, primary amine, secondary amine, tertiary amine and/or ammonium salts, whereby the amine salts are linear or cyclic, of at least partly neutralized homopolymers or copolymers of (meth)acrylic acid, maleic acid, fumaric acid, itaconic acid and derivatives of these acids like esters, or amides, such as methylmethacrylate, methylacrylate, acrylamide, sodium hydrogen phosphate or polyphosphates such as alkalipolyphosphates, carboxymethylcellulose, steric dispersants, comb polymers and/or mixtures thereof, preferably sodium polyacrylate having a molecular weight $M_w$ of from 4 000 to 10 000 g/mol, preferably from 4 000 to 8 000 g/mol and most preferably of about 6 000 g/mol.

According to yet another embodiment of the instant process, the BET specific surface area of i) the calcium carbonate-comprising material in the aqueous suspension mixture obtained in mixing step b) with the proviso that grinding step c) is carried out before mixing step b) or the calcium carbonate-comprising material in the aqueous suspension mixture obtained in grinding step c) with the proviso that grinding step c) is carried out after mixing step b) is between 0.1 and 30.0 $m^2/g$, preferably between 1.0 and 20.0 $m^2/g$, more preferably between 2.0 and 14.0 $m^2/g$ and most preferably between 8.0 and 10.0 $m^2/g$, as measured using nitrogen and the BET method according to ISO 9277, and/or ii) the calcium carbonate-comprising material in the aqueous suspension mixture obtained in mixing step b) with the proviso that grinding step c) is carried out before mixing step b) or the calcium carbonate-comprising material in the aqueous suspension mixture obtained in grinding step c) with the proviso that grinding step c) is carried out after mixing step b) is between 0.1 and 2.0 $m^2/g$, preferably between 0.1 and 1.5 $m^2/g$ and more preferably between 0.2 and 1.0 $m^2/g$ lower than the BET specific surface area of a calcium carbonate-comprising material manufactured by a process using water instead of the second aqueous suspension.

According to one embodiment of the instant process, the Brookfield viscosity of the aqueous suspension mixture obtained in mixing step b) with the proviso that grinding step c) is carried out before mixing step b) or the aqueous suspension mixture obtained in grinding step c) with the proviso that grinding step c) is carried out after mixing step b) is between 50 and 5 000 mPa·s, preferably between 75 and 1 500 mPa·s and more preferably between 150 and 500 mPa·s.

According to another embodiment of the instant process, the calcium carbonate-comprising material in the aqueous suspension mixture obtained in mixing step b) with the proviso that grinding step c) is carried out before mixing step b) or the calcium carbonate-comprising material in the aqueous suspension mixture obtained in grinding step c) with the proviso that grinding step c) is carried out after mixing step b) has a i) top cut particle size $d_{98}$ of ≤50.0 µm, preferably ≤20.0 µm and most preferably ≤10.0 µm, and/or ii) weight median particle size $d_{50}$ between 0.1 and 10.0 µm, preferably between 0.5 and 5.0 µm and most preferably between 1.0 and 2.0 µm.

According to yet another embodiment of the instant process, the solid content i) of the first aqueous suspension is from 30.0 to 78.0 wt.-% and preferably from 50.0 to 76.0 wt.-%, based on the total weight of the aqueous suspension, and/or ii) of the second aqueous suspension is from 30.0 to 40.0 wt.-% and preferably from 34.0 to 43.0 wt.-%, based on the total weight of the aqueous suspension, and/or iii) of the aqueous suspension mixture obtained in mixing step b) with the proviso that grinding step c) is carried out before mixing step b) or the aqueous suspension mixture obtained in grinding step c) with the proviso that grinding step c) is carried out after mixing step b) is from 20.0 to 80.0 wt.-% and preferably from 50.0 to 62.0 wt.-%, based on the total weight of the aqueous suspension.

According to one embodiment of the instant process, at least one of the at least two aqueous suspensions provided in step a) is subjected to a concentration step, preferably mechanical dewatering by means of settling, or forced settling by a centrifuge.

According to another embodiment of the instant process, the calcium carbonate-comprising material is selected from natural calcium carbonate, precipitated calcium carbonate, dolomite and mixtures thereof, preferably natural calcium carbonate such as marble, chalk and/or limestone.

According to yet another embodiment of the instant process, the at least two aqueous suspensions provided in step a) comprise the first and the second aqueous suspension in an amount of more than 10.0 wt.-%, preferably more than 30.0 wt.-%, more preferably more than 60.0 wt.-% and most preferably more than 65.0 wt.-%.

According to one embodiment of the instant process, the at least two aqueous suspensions provided in step a) consist of the first and the second aqueous suspension.

According to another embodiment of the instant process, grinding step c) is carried out after mixing step b).

According to yet another embodiment of the instant process, the process further comprises at least one step d) of concentrating the aqueous suspension mixture obtained in mixing step b) with the proviso that grinding step c) is carried out before mixing step b) or the aqueous suspension mixture obtained in grinding step c) with the proviso that grinding step c) is carried out after mixing step b) to remove at least a portion of water by mechanical means and/or thermal means.

According to one embodiment of the instant process, the process further comprises the steps of e) drying the aqueous suspension obtained in step b) with the proviso that grinding step c) is carried out before mixing step b) or the aqueous suspension mixture obtained in grinding step c) with the proviso that grinding step c) is carried out after mixing step b) or the aqueous suspension mixture obtained in concentrating step d) to obtain a dried calcium carbonate-comprising material; and optionally step f) treating the dried calcium carbonate-comprising material obtained after step e) with at least one dispersing agent and re-diluting it to obtain an aqueous suspension comprising a dispersed calcium carbonate-comprising material, and/or g) treating the dried calcium carbonate-comprising material obtained after step e) with at least one saturated aliphatic linear or branched carboxylic acid and/or with at least one mono-substituted succinic anhydride and/or at least one mono-substituted succinic acid and/or salty reaction product(s) and/or with at least one phosphoric acid ester blend of one or more phosphoric acid mono-ester and/or reaction products thereof and one or more phosphoric acid di-ester and/or reaction products thereof to obtain a hydrophobized calcium carbonate-comprising material.

In the following, it is referred to further details of the present invention and especially the foregoing steps a), b) and c) of the instant process. It is to be understood that these details and embodiments also apply to the calcium carbonate-comprising material itself as well as to the use of said material in any of the disclosed applications.

Characterisation of Step a): Providing at Least Two Aqueous Suspensions

According to step a) of the process of the present invention, at least two aqueous suspensions comprising a calcium carbonate-comprising material are provided.

The term "aqueous" suspension refers to a system, wherein the liquid phase or solvent of the suspension comprises, preferably consists of, water. However, said term does not exclude that the aqueous suspension comprises an organic solvent selected from the group comprising alcohols such as methanol, ethanol, isopropanol, carbonyl-group containing solvents such as ketones, e.g. acetone or aldehydes, esters such as isopropyl acetate, carboxylic acids such as formic acid, sulphoxides such as dimethyl sulphoxide and mixtures thereof. If the aqueous suspension comprises an organic solvent, the aqueous suspension comprises the organic solvent in an amount up to 40.0 wt.-% preferably from 1.0 to 30.0 wt.-% and most preferably from 1.0 to 25.0 wt.-%, based on the total weight of the liquid phase of the aqueous suspension. For example, the liquid phase of the aqueous suspension consists of water. If the liquid phase of the aqueous suspension consists of water, the water to be used can be any water available such as process water, tap water and/or deionised water.

The term "aqueous suspension" in the meaning of the present invention refers to a system comprising at least water as solvent and a calcium carbonate-comprising material and optionally further additives, wherein at least a part of the particles of the calcium carbonate-comprising material are present as undissolved solids in the solvent.

It is one requirement of the instant process that at least two aqueous suspensions comprising a calcium carbonate-comprising material are provided.

The term "at least two" aqueous suspensions in the meaning of the present invention means that two or more aqueous suspensions are provided in step a).

In one embodiment of the present invention, two aqueous suspensions are provided in step a). Alternatively, three or more aqueous suspensions are provided in step a). For example, two or three aqueous suspensions are provided in step a). Preferably, two aqueous suspensions are provided in step a).

Thus, at least a first aqueous suspension and a second aqueous suspension are provided in step a).

In one embodiment of the present invention, the at least two aqueous suspensions provided in step a) comprise the first and the second aqueous suspension in an amount of more than 10.0 wt.-%, preferably more than 30.0 wt.-%, more preferably more than 60.0 wt.-% and most preferably more than 65.0 wt.-%. For example, the at least two aqueous suspensions provided in step a) consist of the first and the second aqueous suspension, i.e. the first and the second aqueous suspension make up 100 wt.-% of the aqueous suspension provided in step a).

It is appreciated that the at least two aqueous suspensions comprising a calcium carbonate-comprising material, i.e. the first aqueous suspension and the second aqueous suspension and each optional aqueous suspension, differ in their solid content and particle size distribution.

It is thus one requirement of the instant invention that the first aqueous suspension has a solid content from 1.0 to 82.0 wt.-%, based on the total weight of the aqueous suspension, and a content of particles having a particle size <2 μm in the range from 1.0 to 30.0 wt.-%. Preferably, the first aqueous suspension has a solid content from 30.0 to 78.0 wt.-%, based on the total weight of the aqueous suspension, and a content of particles having a particle size <2 μm in the range from 1.0 to 30.0 wt.-%. Most preferably, the first aqueous suspension has a solid content from 50.0 to 76.0 wt.-%, based on the total weight of the aqueous suspension, and a content of particles having a particle size <2 μm in the range from 1.0 to 30.0 wt.-%.

In one embodiment of the instant process, the first aqueous suspension has a solid content from 1.0 to 82.0 wt.-%, based on the total weight of the aqueous suspension, and a content of particles having a particle size <2 μm in the range from 5.0 to 30.0 wt.-%. Preferably, the first aqueous suspension has a solid content from 1.0 to 82.0 wt.-%, based on the total weight of the aqueous suspension, and a content of particles having a particle size <2 μm in the range from 10.0 to 30.0 wt.-%. Most preferably, the first aqueous suspension has a solid content from 1.0 to 82.0 wt.-%, based on the total weight of the aqueous suspension, and a content of particles having a particle size <2 μm in the range from 15.0 to 25.0 wt.-%.

Alternatively, the first aqueous suspension has a solid content from 30.0 to 78.0 wt.-%, based on the total weight of the aqueous suspension, and a content of particles having a particle size <2 μm in the range from 5.0 to 30.0 wt.-%. Preferably, the first aqueous suspension has a solid content from 30.0 to 78.0 wt.-%, based on the total weight of the aqueous suspension, and a content of particles having a particle size <2 μm in the range from 10.0 to 30.0 wt.-%. Most preferably, the first aqueous suspension has a solid content from 30.0 to 78.0 wt.-%, based on the total weight of the aqueous suspension, and a content of particles having a particle size <2 μm in the range from 15.0 to 25.0 wt.-%.

For example, the first aqueous suspension has a solid content from 50.0 to 76.0 wt.-%, based on the total weight of the aqueous suspension, and a content of particles having a particle size <2 μm in the range from 5.0 to 30.0 wt.-%. Preferably, the first aqueous suspension has a solid content from 50.0 to 76.0 wt.-%, based on the total weight of the aqueous suspension, and a content of particles having a particle size <2 μm in the range from 10.0 to 30.0 wt.-%. Most preferably, the first aqueous suspension has a solid content from 50.0 to 76.0 wt.-%, based on the total weight of the aqueous suspension, and a content of particles having a particle size <2 μm in the range from 15.0 to 25.0 wt.-%.

In one embodiment of the instant invention the first aqueous suspension has a solid content from 1.0 to 82.0 wt.-%, based on the total weight of the aqueous suspension, and a content of particles having a particle size <1 μm in the range from 1.0 to 20.0 wt.-%. Preferably, the first aqueous suspension has a solid content from 30.0 to 78.0 wt.-%, based on the total weight of the aqueous suspension, and a content of particles having a particle size <1 μm in the range from 1.0 to 20.0 wt.-%. Most preferably, the first aqueous suspension has a solid content from 50.0 to 76.0 wt.-%, based on the total weight of the aqueous suspension, and a content of particles having a particle size <1 μm in the range from 1.0 to 20.0 wt.-%.

In one embodiment of the instant process, the first aqueous suspension has a solid content from 1.0 to 82.0 wt.-%, based on the total weight of the aqueous suspension, and a content of particles having a particle size <1 μm in the range from 2.5 to 20.0 wt.-%. Preferably, the first aqueous suspension has a solid content from 1.0 to 82.0 wt.-%, based on the total weight of the aqueous suspension, and a content of particles having a particle size <1 μm in the range from 2.5 to 15.0 wt.-%. Most preferably, the first aqueous suspension has a solid content from 1.0 to 82.0 wt.-%, based on the total weight of the aqueous suspension, and a content of particles having a particle size <1 μm in the range from 5.0 to 15.0 wt.-%.

Alternatively, the first aqueous suspension has a solid content from 30.0 to 78.0 wt.-%, based on the total weight of the aqueous suspension, and a content of particles having a particle size <1 μm in the range from 2.5 to 20.0 wt.-%. Preferably, the first aqueous suspension has a solid content from 30.0 to 78.0 wt.-%, based on the total weight of the aqueous suspension, and a content of particles having a particle size <1 μm in the range from 2.5 to 15.0 wt.-%. Most preferably, the first aqueous suspension has a solid content from 30.0 to 78.0 wt.-%, based on the total weight of the aqueous suspension, and a content of particles having a particle size <1 μm in the range from 5.0 to 15.0 wt.-%.

For example, the first aqueous suspension has a solid content from 50.0 to 76.0 wt.-%, based on the total weight of the aqueous suspension, and a content of particles having a particle size <1 μm in the range from 2.5 to 20.0 wt.-%. Preferably, the first aqueous suspension has a solid content from 50.0 to 76.0 wt.-%, based on the total weight of the aqueous suspension, and a content of particles having a particle size <1 μm in the range from 2.5 to 15.0 wt.-%. Most preferably, the first aqueous suspension has a solid content from 50.0 to 76.0 wt.-%, based on the total weight of the aqueous suspension, and a content of particles having a particle size <1 μm in the range from 5.0 to 15.0 wt.-%.

Another requirement of the instant invention is that the second aqueous suspension has a solid content from 10.0 to 82.0 wt.-%, based on the total weight of the aqueous suspension, and a content of particles having a particle size <2 μm in the range from >30.0 to 100.0 wt.-%. Preferably, the second aqueous suspension has a solid content from 30.0 to 40.0 wt.-%, based on the total weight of the aqueous suspension, and a content of particles having a particle size <2 μm in the range from >30.0 to 100.0 wt.-%. Most preferably, the second aqueous suspension has a solid content from 34.0 to 43.0 wt.-%, based on the total weight of the aqueous suspension, and a content of particles having a particle size <2 μm in the range from >30.0 to 100.0 wt.-%.

In one embodiment of the instant process, the second aqueous suspension has a solid content from 10.0 to 82.0 wt.-%, based on the total weight of the aqueous suspension, and a content of particles having a particle size <2 μm in the range from >40.0 to 90.0 wt.-%. Preferably, the second aqueous suspension has a solid content from 10.0 to 82.0 wt.-%, based on the total weight of the aqueous suspension, and a content of particles having a particle size <2 μm in the range from 50.0 to 80.0 wt.-%. Most preferably, the second aqueous suspension has a solid content from 10.0 to 82.0 wt.-%, based on the total weight of the aqueous suspension, and a content of particles having a particle size <2 μm in the range from 60.0 to 70.0 wt.-%.

Alternatively, the second aqueous suspension has a solid content from 30.0 to 40.0 wt.-%, based on the total weight of the aqueous suspension, and a content of particles having a particle size <2 μm in the range from 40.0 to 90.0 wt.-%. Preferably, the second aqueous suspension has a solid content from 30.0 to 40.0 wt.-%, based on the total weight of the aqueous suspension, and a content of particles having a particle size <2 μm in the range from 50.0 to 80.0 wt.-%. Most preferably, the second aqueous suspension has a solid content from 30.0 to 40.0 wt.-%, based on the total weight of the aqueous suspension, and a content of particles having a particle size <2 μm in the range from 60.0 to 70.0 wt.-%.

For example, the second aqueous suspension has a solid content from 34.0 to 43.0 wt.-%, based on the total weight of the aqueous suspension, and a content of particles having a particle size <2 μm in the range from 40.0 to 90.0 wt.-%. Preferably, the second aqueous suspension has a solid content from 34.0 to 43.0 wt.-%, based on the total weight of the aqueous suspension, and a content of particles having a particle size <2 μm in the range from 50.0 to 80.0 wt.-%. Most preferably, the second aqueous suspension has a solid content from 34.0 to 43.0 wt.-%, based on the total weight of the aqueous suspension, and a content of particles having a particle size <2 µm in the range from 60.0 to 70.0 wt.-%.

In one embodiment of the instant invention the second aqueous suspension has a solid content from 10.0 to 82.0 wt.-%, based on the total weight of the aqueous suspension, and a content of particles having a particle size <1 µm in the range from 10.0 to 50.0 wt.-%. Preferably, the second aqueous suspension has a solid content from 30.0 to 40.0 wt.-%, based on the total weight of the aqueous suspension, and a content of particles having a particle size <1 µm in the range from 10.0 to 50.0 wt.-%. Most preferably, the second aqueous suspension has a solid content from 34.0 to 43.0 wt.-%, based on the total weight of the aqueous suspension, and a content of particles having a particle size <1 µm in the range from 10.0 to 50.0 wt.-%.

In one embodiment of the instant process, the second aqueous suspension has a solid content from 10.0 to 82.0 wt.-%, based on the total weight of the aqueous suspension, and a content of particles having a particle size <1 µm in the range from 20.0 to 50.0 wt.-%. Preferably, the second aqueous suspension has a solid content from 10.0 to 82.0 wt.-%, based on the total weight of the aqueous suspension, and a content of particles having a particle size <1 µm in the range from 25.0 to 40.0 wt.-%. Most preferably, the second aqueous suspension has a solid content from 10.0 to 82.0 wt.-%, based on the total weight of the aqueous suspension, and a content of particles having a particle size <1 µm in the range from 27.5 to 35.0 wt.-%.

Alternatively, the second aqueous suspension has a solid content from 30.0 to 40.0 wt.-%, based on the total weight of the aqueous suspension, and a content of particles having a particle size <1 µm in the range from 20.0 to 50.0 wt.-%. Preferably, the second aqueous suspension has a solid content from 30.0 to 40.0 wt.-%, based on the total weight of the aqueous suspension, and a content of particles having a particle size <1 µm in the range from 25.0 to 40.0 wt.-%. Most preferably, the second aqueous suspension has a solid content from 30.0 to 40.0 wt.-%, based on the total weight of the aqueous suspension, and a content of particles having a particle size <1 µm in the range from 27.5 to 35.0 wt.-%.

For example, the second aqueous suspension has a solid content from 34.0 to 43.0 wt.-%, based on the total weight of the aqueous suspension, and a content of particles having a particle size <1 µm in the range from 20.0 to 50.0 wt.-%. Preferably, the second aqueous suspension has a solid content from 34.0 to 43.0 wt.-%, based on the total weight of the aqueous suspension, and a content of particles having a particle size <1 µm in the range from 25.0 to 40.0 wt.-%. Most preferably, the second aqueous suspension has a solid content from 34.0 to 43.0 wt.-%, based on the total weight of the aqueous suspension, and a content of particles having a particle size <1 µm in the range from 27.5 to 35.0 wt.-%.

According to one embodiment of the inventive process the at least two aqueous suspensions provided in step a) are obtained by up-concentrating and separating different fractions of an aqueous suspension. For example, the first aqueous suspension of the at least two aqueous suspensions provided in step a) is obtained by partially dewatering an aqueous suspension to the desired solid content. Preferably, the aqueous suspension can be partially dewatered such that the obtained cake forms the first aqueous suspension having a solid content from 1.0 to 82.0 wt.-%, based on the total weight of the aqueous suspension, and a content of particles having a particle size <2 µm in the range from 1.0 to 30.0 wt.-%.

In one embodiment of the instant process, the second aqueous suspension of the at least two aqueous suspensions provided in step a) is obtained by partially dewatering the supernatant separated from the first aqueous suspension to the desired solid content. Preferably, the supernatant obtained by partially dewatering the supernatant separated from the first aqueous suspension can be further partially dewatered such that the obtained cake forms the second aqueous suspension having a solid content from 10.0 to 82.0 wt.-%, based on the total weight of the aqueous suspension, and a content of particles having a particle size <2 µm in the range from >30.0 to 100.0 wt.-%.

The solids content of the aqueous suspensions can be adjusted by the methods known to the skilled person. To adjust the solids content of an aqueous suspension, the aqueous suspension may be partially dewatered by a settling, filtration, centrifugation or thermal separation process. For example, the first aqueous suspension of the at least two aqueous suspensions provided in step a) is obtained by partially dewatering an aqueous suspension by centrifugation to the desired solid content and/or the second aqueous suspension of the at least two aqueous suspensions provided in step a) is obtained by partially dewatering the supernatant separated from the first aqueous suspension by settling to the desired solid content.

The partial dewatering by centrifugation and/or settling can be carried out by using methods well known to the skilled person.

The at least two aqueous suspensions comprise a calcium carbonate-comprising material. In particular, the calcium carbonate-comprising material comprises calcium carbonate-comprising particles.

According to one embodiment of the present invention, the calcium carbonate-comprising material being part of the at least two aqueous suspensions is selected from among natural calcium carbonate, precipitated calcium carbonate, dolomite and mixtures thereof.

"Ground calcium carbonate" (GCC) in the meaning of the present invention is a calcium carbonate obtained from natural sources, such as limestone, marble and/or chalk, and processed through a wet and/or dry treatment such as grinding, screening and/or fractionating, for example by a cyclone or classifier.

A ground calcium carbonate (GCC) may feature, e.g. one or more of marble, limestone and/or chalk. According to one embodiment of the present invention the GCC is obtained by dry grinding. According to another embodiment of the present invention the GCC is obtained by wet grinding and subsequent drying.

In general, the grinding step can be carried out with any conventional grinding device, for example, under conditions such that refinement predominantly results from impacts with a secondary body, i.e. in one or more of: a ball mill, a rod mill, a vibrating mill, a roll crusher, a centrifugal impact mill, a vertical bead mill, an attrition mill, a pin mill, a hammer mill, a pulveriser, a shredder, a de-clumper, a knife cutter, or other such equipment known to the skilled man. In case the calcium carbonate-comprising particles comprise wet ground calcium carbonate-containing particles, the grinding step may be performed under conditions such that autogenous grinding takes place and/or by horizontal ball milling, and/or other such processes known to the skilled man. The wet processed ground calcium carbonate-comprising particles thus obtained may be washed and dewatered by well known processes, e.g. by flocculation, filtration or forced evaporation prior to drying. The subsequent step of drying may be carried out in a single step such as spray drying, or in at least two steps. It is also common that such calcium carbonate-comprising particles undergo a beneficiation step (such as a flotation, bleaching or magnetic separation step) to remove impurities.

"Dolomite" in the meaning of the present invention is a carbonatic calcium-magnesium-mineral having the chemical composition of $CaMg(CO_3)_2$ ("$CaCO_3.MgCO_3$"). Dolomite mineral contains at least 30.0 wt.-% $MgCO_3$, based on the total weight of dolomite, preferably more than 35.0 wt.-%, more preferably more than 40.0 wt.-% $MgCO_3$.

"Precipitated calcium carbonate" (PCC) in the meaning of the present invention is a synthesized material, generally obtained by precipitation following reaction of carbon dioxide and lime in an aqueous environment or by precipitation of a calcium and carbonate ion source in water.

A precipitated calcium carbonate (PCC) may feature, e.g. one or more of aragonitic, vateritic and/or calcitic mineralogical morphological forms. The aragonitic morphology is commonly in the acicular form, whereas vateritic morphology belongs to the hexagonal crystal system. The calcitic morphology can form scalenohedral, prismatic, spheral and rhombohedral forms. PCC can be produced in different ways, e.g. by precipitation with carbon dioxide, the lime soda process, or the Solvay process in which PCC is a by-product of ammonia production. The obtained PCC slurry can be mechanically dewatered and dried.

For example, the calcium carbonate-comprising material is GCC being selected from the group comprising marble, chalk, limestone and mixtures thereof. In one embodiment, the calcium carbonate-comprising material is GCC being selected from marble or chalk, preferably marble.

In addition to calcium carbonate, the calcium carbonate-comprising material may comprise further metal oxides such as titanium dioxide and/or aluminium trioxide, metal hydroxides such as aluminium tri-hydroxide, metal salts such as sulfates e.g. gypsum or satin white, silicates such as talc and/or kaolin clay and/or mica, carbonates such as magnesium carbonate and/or and mixtures thereof.

According to one embodiment of the present invention, the calcium carbonate-comprising material contains at least 50.0 wt.-%, preferably at least 70.0 wt.-%, more preferably at least 80.0 wt.-%, even more preferably at least 90.0 wt.-%, and most preferably from 90.0 to 98.0 wt.-% of calcium carbonate, based on the total weight of said calcium carbonate-comprising material.

According to one embodiment of the present invention, the calcium carbonate-comprising material has a weight median particle size $d_{50}$ from 0.1 to 100.0 µm, from 0.25 to 50.0 µm, or from 0.3 to 25.0 µm, preferably from 2.5 to 20.0 µm, as measured by Sedigraph 5120 or Sedigraph 5100.

In one embodiment of the present invention, the weight median particle size $d_{50}$ of the calcium carbonate-comprising material in the first aqueous suspension and of the calcium carbonate-comprising material in the second aqueous suspension is the same. Alternatively, the weight median particle size $d_{50}$ of the calcium carbonate-comprising material in the first aqueous suspension and of the calcium carbonate-comprising material in the second aqueous suspension is different. Preferably, the weight median particle size $d_{50}$ of the calcium carbonate-comprising material in the first aqueous suspension and of the calcium carbonate-comprising material in the second aqueous suspension is the same.

It is appreciated that the first aqueous suspension and the second aqueous suspension preferably comprise the same calcium carbonate-comprising material, i.e. the calcium carbonate-comprising material in the first aqueous suspension is selected from among natural calcium carbonate, precipitated calcium carbonate, dolomite and mixtures thereof, and the calcium carbonate-comprising material in the second aqueous suspension is selected from the same material.

Alternatively, the calcium carbonate-comprising material in the first aqueous suspension and the calcium carbonate-comprising material in the second aqueous suspension are independently selected from among natural calcium carbonate, precipitated calcium carbonate, dolomite and mixtures thereof.

In one embodiment of the present invention, at least one of the at least two aqueous suspensions provided in step a) is subjected to a concentration step, preferably mechanical dewatering by means of settling, or forced settling by a centrifuge. Preferably, the first aqueous suspension of the at least two aqueous suspensions provided in step a) is subjected to a concentration step, preferably mechanical dewatering by means of settling, or forced settling by a centrifuge.

For adjusting the solid content of at least one of the at least two aqueous suspensions provided in step a), it is also possible that at least one of the at least two aqueous suspensions provided in step a) is obtained in a concentration step, preferably mechanical dewatering by means of settling, or forced settling by a centrifuge. For example, the first aqueous suspension of the at least two aqueous suspensions provided in step a) is obtained in a concentration step, preferably mechanical dewatering by means of settling, or forced settling by a centrifuge.

Characterisation of Step b): Mixing the at Least Two Aqueous Suspensions

According to step b) of the process of the present invention, the at least two aqueous suspensions are mixed to obtain an aqueous suspension mixture.

According to one embodiment of the inventive process, the first aqueous suspension and each optional further aqueous suspension is added to the second aqueous suspension. According to another embodiment of the inventive process the second aqueous suspension and each optional further aqueous suspension is added to the first aqueous suspension.

In one embodiment of the present invention, a sufficient mixing may be achieved by shaking the aqueous suspension or by agitation, which may provide a more thorough mixing. In one embodiment of the present invention, mixing step b) is carried out under agitation to ensure a thorough mixing of the at least two aqueous suspensions. Such agitation can be carried out continuously or discontinuously. The skilled person will adapt the mixing conditions such as the mixing speed and temperature according to his process equipment.

The mixing step b) may be carried out at room temperature, i.e. at 20° C.±2° C., or at other temperatures. According to one embodiment mixing step b) is carried out at a temperature from 5 to 140° C., preferably from 10 to 110° C., and most preferably from 20 to 105° C. Heat may be introduced by internal shear or by an external source or a combination thereof.

Characterisation of Step c): Grinding

According to step c) of the process of the present invention, the aqueous suspension mixture obtained in mixing step b) and/or at least one of the at least two aqueous suspensions provided in step a) before mixing step b) is carried out, is/are ground.

The grinding step c) is preferably carried out by wet grinding.

The term "wet grinding" in the meaning of the process according to the present invention refers to the comminution (e.g. in a ball mill) of solid material (e.g. of mineral origin) in the presence of water meaning that said material is in form of an aqueous suspension.

In general, the grinding step c) can be carried out with any conventional grinding device, for example, under conditions such that refinement predominantly results from impacts with a secondary body, i.e. in one or more of: a ball mill, a rod mill, a vibrating mill, a roll crusher, a centrifugal impact mill, a vertical bead mill, an attrition mill, a pin mill, a hammer mill, a pulveriser, a shredder, a de-clumper, a knife cutter, or other such equipment known to the skilled man. The grinding step c) may be also performed under conditions such that autogenous grinding takes place and/or by horizontal and or vertical ball milling, and/or other such processes known to the skilled man.

For the purposes of the present invention, any suitable mill known in the art may be used. However, said grinding unit preferably takes place in a ball mill. It has to be noted that grinding step c) is carried out by using at least one grinding unit, i.e. it is also possible to use a series of grinding units which may, for example, be selected from ball mills, semi-autogenous mills, or autogenous mills.

The amount of water being present in the aqueous suspension to be ground may be expressed by the total moisture content which is based on the total weight of said aqueous suspension. Typically, wet grinding processes are carried out using aqueous suspensions having a total moisture content ranging from 10.0 to 99.0 wt.-%.

Preferably, the grinding step c) is carried out at high solids contents, i.e. at low total moisture contents, for example at a total moisture content ranging from 10 to 80.0 wt.-%, based on the total weight of said aqueous suspension.

According to one embodiment, preferably when the grinding step c) is carried out before the mixing step b) the total moisture content in the first aqueous suspension of grinding step c) ranges from 10 to 35.0 wt.-%, preferably from 15.0 to 30.0 wt.-%, and more preferably from 20.0 to 27.0 wt.-%, based on the total weight of the aqueous suspension.

According to one embodiment, preferably when the grinding step c) is carried out before the mixing step b) the total moisture content in the second aqueous suspension of grinding step c) ranges from 40.0 to 80.0 wt.-%, preferably from 50.0 to 70.0 wt.-%, and more preferably from 55.0 to 65.0 wt.-%, based on the total weight of the aqueous suspension.

When grinding step c) is carried out after mixing step b) the total moisture content in the aqueous suspension of grinding step c) ranges from 30 to 60 wt.-%, preferably from 35 to 50 wt.-%.

Additionally or alternatively, it is advantageous to carry out the grinding step c) at a specific ratio of calcium carbonate-comprising material to grinding beads. For example, the weight ratio of calcium carbonate-comprising material to grinding beads (wt./wt.) in the grinding unit is from 2:1 to 10:1, preferably from 3:1 to 8:1, more preferably from 3:1 to 6:1 and most preferably from 4:1 to 6:1. Most preferably, the weight ratio of calcium carbonate-comprising material to grinding beads (wt./wt.) in the grinding unit is about 5:1.

The grinding beads can be any material suitable for grinding aqueous suspensions of calcium carbonate-comprising materials. For example, the grinding beads can be melt fused grinding beads consisting of 68 wt.-% baddeleyite and 32 wt.-% amorphous silica, based on the total weight of the grinding beads.

For the grinding step c) a temperature ranging from 10° C. to 150° C. is particularly suitable. Preferably, grinding step c) is carried out at a temperature ranging from 10 to 80° C. or from 10° C. to 50° C. Most preferably, grinding step c) is carried out at room temperature, i.e. at about 20° C.±3° C.

According to one embodiment of the present invention, grinding step c) is carried out for at least 1 min, preferably for at least 10 min, e.g. for at least 15 min, 30 min, or 45 min. Alternatively, grinding step c) is carried out for at most 10 hours, preferably for at most 7 hours, e.g. for at most 5 hours, 3 hours, or 2 hours. For example, is carried out for a period ranging from 1 min to 10 hours, e.g. from 10 min to 7 hours, 15 min to 5 hours, 30 min to 3 hours or 45 min to 2 hours.

Additionally or alternatively, the grinding step c) is carried out at a milling speed ranging from 100 rpm to 10 000 rpm, preferably from 1 000 rpm to 7 500 rpm, more preferably from 1 500 rpm to 5 000 rpm and most preferably from 1 500 rpm to 4 000 rpm.

The grinding can be carried out before and/or after mixing step b). In other words, process step c) can be carried out in that the aqueous suspension mixture obtained in mixing step b) is ground. Additionally or alternatively, process step c) is carried out in that at least one of the at least two aqueous suspensions provided in step a) is ground before mixing step b) is carried out.

In one embodiment of the present invention, process step c) is carried out such that at least one of the at least two aqueous suspensions provided in step a) is ground before mixing step b) is carried out. For example, the first aqueous suspension and/or the second aqueous suspension and/or each optional further aqueous suspension is/are ground before mixing step b) is carried out. Preferably, the first aqueous suspension or the second aqueous suspension or each optional further aqueous suspension is ground before mixing step b) is carried out.

In case grinding step c) is carried out before mixing step b), it is preferred that the aqueous suspension of the at least two aqueous suspensions provided in step a) is ground providing the lowest content of particles having a particle size <2 µm. Thus, in this embodiment it is preferred that the first aqueous suspension is ground before mixing step c) is carried out.

It has been found by the inventors that process step c) is preferably carried out in that the aqueous suspension mixture obtained in mixing step b) is ground. Thus, grinding step c) is preferably carried out after mixing step b).

According to one embodiment, at least one dispersing agent is added to at least one of the at least two aqueous suspensions provided in step a) and/or to the aqueous suspension mixture obtained in mixing step b).

The expression "at least one" dispersing agent means that one or more kind of a dispersing agent may be added to at least one of the at least two aqueous suspensions provided in step a) and/or to the aqueous suspension mixture obtained in mixing step b).

According to one preferred embodiment of the present invention, only one kind of a dispersing agent is added to at least one of the at least two aqueous suspensions provided in step a) and/or to the aqueous suspension mixture obtained in mixing step b). According to another embodiment of the present invention, two or more kinds of a dispersing agent are added to at least one of the at least two aqueous suspensions provided in step a) and/or to the aqueous suspension mixture obtained in mixing step b). For example, two or three kinds of a dispersing agent are added to at least one of the at least two aqueous suspensions provided in step a) and/or to the aqueous suspension mixture obtained in mixing step b). Preferably, two kinds of a dispersing agent are added to at least one of the at least two aqueous suspensions provided in step a) and/or to the aqueous suspension mixture obtained in mixing step b). Alternatively, only one kind of a dispersing agent is added to at least one of the at least two aqueous suspensions provided in step a) and/or to the aqueous suspension mixture obtained in mixing step b).

In one embodiment of the instant process, the at least one dispersing agent is added to at least one of the at least two aqueous suspensions provided in step a) and/or to the aqueous suspension mixture obtained in mixing step b). For example, the at least one dispersing agent is added to at least one of the at least two aqueous suspensions provided in step a) or to the aqueous suspension mixture obtained in mixing step b). It has been found by the inventors that the at least one dispersing agent is preferably added to at least one of the at least two aqueous suspensions provided in step a) and to the aqueous suspension mixture obtained in mixing step b).

Conventional dispersing agents known to the skilled person can be used. According to another embodiment the at least one dispersing agent is selected from the group consisting of sodium, potassium, calcium, magnesium, lithium, strontium, primary amine, secondary amine, tertiary amine and/or ammonium salts, whereby the amine salts are linear or cyclic, of at least partly neutralized homopolymers or copolymers of (meth)acrylic acid, maleic acid, fumaric acid, itaconic acid and derivatives of these acids, preferably esters or amides such as methylmethacrylate, methylacrylate, acrylamide, sodium hydrogen phosphate or polyphosphates such as alkalipolyphosphates, carboxymethylcellulose, steric dispersants, comb polymers and/or mixtures thereof, preferably sodium polyacrylate having a molecular weight $M_w$ of from 4 000 to 10 000 g/mol, preferably from 4 000 to 8 000 g/mol and most preferably of about 6 000 g/mol.

In one embodiment of the process according to the present invention, the Brookfield Viscosity of at least one of the at least two aqueous suspensions provided in step a) and/or the aqueous suspension mixture obtained in mixing step b) is adjusted to <2 000 mPa·s, preferably <1 000 mPa·s, more preferably <750 mPa·s, even more preferably <500 mPa·s and most preferably <250 mPa·s by addition of a dispersing agent.

A variant of the process according to the invention is characterized in that it is performed in absence of any dispersing agent during process steps a), b) and c).

This process is also characterized in that if a dispersing agent is present, it is present in a weight % relative to the total dry calcium carbonate-comprising material ranging from 0.001 wt.-% to 5.0 wt.-%, preferably from 0.001 wt.-% to 2.0 wt.-%, and most preferably from 0.05 wt.-% to 1.0 wt.-%, for example from 0.16 wt.-% to 0.22 wt.-%.

In one embodiment of the present invention, a dispersing agent is added to at least one of the at least two aqueous suspensions provided in step a) and/or to the aqueous suspension mixture obtained in mixing step b) in case the solid content of the corresponding aqueous suspension is ≥20.0 wt.-% and most preferably from 20.0 to 82.0 wt.-%, based on the total weight of the corresponding aqueous suspension. For example, a dispersing agent is added to at least one of the at least two aqueous suspensions provided in step a) and/or to the aqueous suspension mixture obtained in mixing step b) in an amount ranging from 0.001 wt.-% to 5.0 wt.-%, preferably from 0.001 wt.-% to 2.0 wt.-%, and most preferably from 0.05 wt.-% to 1.0 wt.-%, for example from 0.16 wt.-% to 0.22 wt.-%, based on the total dry weight of calcium carbonate-comprising material, in case the solid content of the corresponding aqueous suspension is ≥20.0 wt.-% and most preferably from 20.0 to 82.0 wt.-%, based on the total weight of the corresponding aqueous suspension.

According to an optional embodiment of the present invention, the process further comprises at least one step d) of concentrating the aqueous suspension mixture obtained in mixing step b) with the proviso that grinding step c) is carried out before mixing step b) or the aqueous suspension mixture obtained in grinding step c) with the proviso that grinding step c) is carried out after mixing step b).

The solids content of the obtained aqueous suspension mixture obtained in mixing step b) with the proviso that grinding step c) is carried out before mixing step b) or the aqueous suspension mixture obtained in grinding step c) with the proviso that grinding step c) is carried out after mixing step b) can be adjusted by concentrating methods known to the skilled person. The concentrating of the corresponding aqueous suspension mixture may be achieved by means of a thermal process, for example in an evaporator, or by means of a mechanical process, for example in a filter press such as nanofiltration, and/or in a centrifuge.

The solids content of the corresponding aqueous suspension mixture obtained by the process of the present invention can be concentrated by removing at least a portion of the water so that the solids content is from 20.0 to 80.0 wt.-%, more preferably from 30.0 to 70.0 wt.-%, most preferably from 40 to 65.0 wt.-%, based on the total weight of the corresponding aqueous suspension mixture. According to one preferred embodiment, the solids content of the corresponding aqueous suspension mixture is concentrated to a medium solid content so that it is from 50.0 to 62.0 wt.-%, based on the total weight of the corresponding aqueous suspension mixture.

According to one optional embodiment of the present invention, the step of concentrating the corresponding aqueous suspension mixture obtained by the process of the present invention is carried out such that a dry product is obtained.

In one preferred embodiment of the present invention, the process of the present invention may lead directly to a solid content in the aqueous suspension mixture obtained in mixing step b) with the proviso that grinding step c) is carried out before mixing step b) or the aqueous suspension mixture obtained in grinding step c) with the proviso that grinding step c) is carried out after mixing step b) from 20.0 to 80.0 wt.-% and preferably from 50.0 to 62.0 wt.-%, based on the total weight of the aqueous suspension, which means that an additional concentration step is not implemented in the process of the present invention.

In another embodiment of the instant process, the process further comprises the steps of
  e) drying the aqueous suspension obtained in step b) with the proviso that grinding step c) is carried out before mixing step b) or the aqueous suspension mixture obtained in grinding step c) with the proviso that grinding step c) is carried out after mixing step b) or the aqueous suspension mixture obtained in concentrating step d) to remove at least a portion of water to obtain a partially dewatered calcium carbonate-comprising material or to obtain a dried calcium carbonate-comprising material; and optionally
  f) treating the dried calcium carbonate-comprising material obtained after step e) with at least one dispersing agent and re-diluting it to obtain an aqueous suspension comprising a dispersed calcium carbonate-comprising material, and/or g) treating the dried calcium carbonate-comprising material obtained after step e) with at least one saturated aliphatic linear or branched carboxylic acid and/or with at least one mono-substituted succinic anhydride and/or at least one mono-substituted succinic acid and/or salty reaction product(s) and/or with at least one phosphoric acid ester blend of one or more phosphoric acid mono-ester and/or reaction products thereof and one or more phosphoric acid di-ester and/or reaction products thereof to obtain a hydrophobized calcium carbonate-comprising material.

The methods for treating a partially dewatered and/or dried calcium carbonate-comprising with at least one mono-substituted succinic anhydride and/or at least one mono-substituted succinic acid and/or salty reaction product(s) and/or with at least one phosphoric acid ester blend of one or more phosphoric acid mono-ester and/or reaction products thereof and one or more phosphoric acid di-ester and/or reaction products thereof and suitable compounds for coating are described in EP 2 722 368 A1 and EP 2 770 017 A1, which are thus incorporated herewith by references.

Suitable saturated aliphatic linear or branched carboxylic acids for treating the dried calcium carbonate-comprising material and/or partially dewatered calcium carbonate-comprising material are for example aliphatic linear or branched carboxylic acids having between 5 and 24 carbon atoms during and/or before and/or after drying. Preferably, the dried calcium carbonate-comprising material and/or partially dewatered calcium carbonate-comprising material is treated with an aliphatic linear or branched carboxylic acid having between 5 and 24 carbon atoms before or after drying. More preferably, the dried calcium carbonate-comprising material and/or partially dewatered calcium carbonate-comprising material is treated with an aliphatic linear or branched carboxylic acid having between 5 and 24 carbon atoms before drying.

The aliphatic linear or branched carboxylic acid in the meaning of the present invention may be selected from one or more straight chain, branched chain, saturated, unsaturated and/or alicyclic carboxylic acids. Preferably, the aliphatic linear or branched carboxylic acid is a monocarboxylic acid, i.e. the aliphatic linear or branched carboxylic acid is characterized in that a single carboxyl group is present. Said carboxyl group is placed at the end of the carbon skeleton.

In one embodiment of the present invention, the aliphatic linear or branched carboxylic acid is selected from saturated unbranched carboxylic acids, that is to say the aliphatic linear or branched carboxylic acid is preferably selected from the group of carboxylic acids consisting of pentanoic acid, hexanoic acid, heptanoic acid, octanoic acid, nonanoic acid, decanoic acid, undecanoic acid, lauric acid, tridecanoic acid, myristic acid, pentadecanoic acid, palmitic acid, heptadecanoic acid, stearic acid, nonadecanoic acid, arachidic acid, heneicosylic acid, behenic acid, tricosylic acid, lignoceric acid and mixtures thereof.

In another embodiment of the present invention, the aliphatic linear or branched carboxylic acid is selected from the group consisting of octanoic acid, decanoic acid, lauric acid, myristic acid, palmitic acid, stearic acid, arachidic acid and mixtures thereof. Preferably, the aliphatic linear or branched carboxylic acid is selected from the group consisting of myristic acid, palmitic acid, stearic acid and mixtures thereof.

For example, the aliphatic linear or branched carboxylic acid is stearic acid.

The Calcium Carbonate-Comprising Material

The inventors surprisingly found that according to the process of the present invention, a calcium carbonate-comprising material is obtainable, wherein the BET specific surface area of the final product is lower as compared to conventional processes using water instead of the second aqueous suspension.

Thus, the BET specific surface area of the calcium carbonate-comprising material in the aqueous suspension mixture obtained in mixing step b), with the proviso that grinding step c) is carried out before mixing step b), is between 0.1 and 30.0 $m^2/g$, preferably between 1.0 and 20.0 $m^2/g$, more preferably between 2.0 and 14.0 $m^2/g$ and most preferably between 8.0 and 10.0 $m^2/g$, as measured using nitrogen and the BET method according to ISO 9277. Additionally or alternatively, the BET specific surface area of the calcium carbonate-comprising material in the aqueous suspension mixture obtained in mixing step b) with the proviso that grinding step c) is carried out before mixing step b) is between 0.1 and 2.0 $m^2/g$, preferably between 0.1 and 1.5 $m^2/g$ and more preferably between 0.2 and 1.0 $m^2/g$ lower than the BET specific surface area of a calcium carbonate-comprising material manufactured by a process using water instead of the second aqueous suspension.

In an alternative embodiment, if the calcium carbonate-comprising material in the aqueous suspension mixture is obtained in grinding step c), with the proviso that grinding step c) is carried out after mixing step b), the BET specific surface area of the calcium carbonate-comprising material in the aqueous suspension mixture obtained in grinding step c) is between 0.1 and 30.0 $m^2/g$, preferably between 1.0 and 20.0 $m^2/g$, more preferably between 2.0 and 14.0 $m^2/g$ and most preferably between 8.0 and 10.0 $m^2/g$, as measured using nitrogen and the BET method according to ISO 9277.

Additionally or alternatively, if the calcium carbonate-comprising material in the aqueous suspension mixture is obtained in grinding step c), with the proviso that grinding step c) is carried out after mixing step b), the BET specific surface area of the calcium carbonate-comprising material in the aqueous suspension mixture obtained in grinding step c) is between 0.1 and 2.0 $m^2/g$, preferably between 0.1 and 1.5 $m^2/g$ and more preferably between 0.2 and 1.0 $m^2/g$ lower than the BET specific surface area of a calcium carbonate-comprising material manufactured by a process using water instead of the second aqueous suspension.

In one embodiment of the instant process, the Brookfield viscosity of the aqueous suspension mixture obtained in mixing step b) with the proviso that grinding step c) is carried out before mixing step b) is between 50 and 5 000 mPa·s, preferably between 75 and 1 500 mPa·s and more preferably between 150 and 500 mPa·s. Alternatively, if the aqueous suspension mixture is obtained in grinding step c), with the proviso that grinding step c) is carried out after mixing step b), the Brookfield viscosity of the aqueous suspension mixture obtained in grinding step c) is between 50 and 5 000 mPa·s, preferably between 75 and 1 500 mPa·s and more preferably between 150 and 500 mPa·s.

In one embodiment of the present invention, the calcium carbonate-comprising material in the aqueous suspension mixture obtained in mixing step b) with the proviso that grinding step c) is carried out before mixing step b) has a top cut particle size $d_{98}$ of ≤50.0 μm, preferably ≤20.0 μm and most preferably ≤10.0 μm. Additionally or alternatively, the calcium carbonate-comprising material in the aqueous suspension mixture obtained in mixing step b) with the proviso that grinding step c) is carried out before mixing step b) has a weight median particle size $d_{50}$ between 0.1 and 10.0 µm, preferably between 0.5 and 5.0 µm and most preferably between 1.0 and 2.0 µm.

In an alternative embodiment, if the calcium carbonate-comprising material in the aqueous suspension mixture is obtained in grinding step c), with the proviso that grinding step c) is carried out after mixing step b), the calcium carbonate-comprising material has a top cut particle size $d_{98}$ of ≤50.0 µm, preferably ≤20.0 µm and most preferably ≤10.0 µm. Additionally or alternatively, if the calcium carbonate-comprising material in the aqueous suspension mixture is obtained in grinding step c), with the proviso that grinding step c) is carried out after mixing step b), the calcium carbonate-comprising material has a weight median particle size $d_{50}$ between 0.1 and 10.0 µm, preferably between 0.5 and 5.0 µm and most preferably between 1.0 and 2.0 µm.

In view of the advantageous properties of the calcium carbonate-comprising material, especially the BET specific surface area of the final product being lower as compared to conventional processes using water instead of the second aqueous suspension, the present invention is further directed to the calcium carbonate-comprising material obtained by the instant process.

The inventive calcium carbonate-comprising material may be used for paper filler and paper coating applications, in plastics applications, in paints, in adhesive, in sealings, in concrete, in agriculture applications, in food applications, in cosmetic applications or in pharmaceutical applications.

As the calcium carbonate-comprising material has a low BET specific surface area, it may advantageously be used in paper coatings in order to adjust the printing and optical properties of a coated paper. Furthermore, the calcium carbonate-comprising material may also be used in paints which may lead to improved optical properties of surfaces being treated with such paints.

The use of the calcium carbonate-comprising material according to the present invention as a filler material in plastic applications may also be of particular advantage. For example, said calcium carbonate-comprising material may be used in thermoplastic polymers, such as polyvinyl chloride, polyolefins and polystyrene.

The following figures, examples and tests will illustrate the present invention, but are not intended to limit the invention in any way.

EXPERIMENTAL SECTION

1. Measurement Methods

In the following the measurement methods implemented in the examples are described.

Particle Size Distribution (Mass % Particles with a Diameter <X) and Weight Median Particle Size ($d_{50}$) of a Particulate Material Weight grain diameter and grain diameter mass distribution of a particulate material were determined via the sedimentation method, i.e. an analysis of sedimentation behaviour in a gravitational field. The measurement was made with a Sedigraph™ 5120 or a Sedigraph™ 5100 of Micromeritics Instrument Corporation.

The method and the instrument are known to the skilled person and are commonly used to determine grain size of fillers and pigments. The measurement is carried out in an aqueous solution of 0.1 wt.-% $Na_4P_2O_7$. The samples are dispersed using a high speed stirrer and supersonics.

BET Specific Surface Area of a Material

Throughout the present document, the specific surface area (in $m^2/g$) of a particulate material was determined using the BET method (using nitrogen as adsorbing gas), which is well known to the skilled man (ISO 9277:1995). The total surface area (in $m^2$) of the particulate material is then obtained by multiplication of the specific surface area and the mass (in g) of the particulate material. The method and the instrument are known to the skilled person and are commonly used to determine the specific surface of particulate materials.

Suspension pH Measurement

The pH of a suspension is measured at 25° C. using a Mettler Toledo Seven Easy pH meter and a Mettler Toledo InLab® Expert Pro pH electrode. A three point calibration (according to the segment method) of the instrument is first made using commercially available buffer solutions having pH values of 4, 7 and 10 at 20° C. (from Aldrich). The reported pH values are the endpoint values detected by the instrument (the endpoint is when the measured signal differs by less than 0.1 mV from the average over the last 6 seconds).

Brookfield Viscosity

For the purpose of the present invention, the term "viscosity" or "Brookfield viscosity" refers to Brookfield viscosity. The Brookfield viscosity is for this purpose measured by a Brookfield (Type RVT) viscometer at 25° C.±1° C. at 100 rpm using an appropriate spindle of the Brookfield RV-spindle set and is specified in mPa·s. Based on his technical knowledge, the skilled person will select a spindle from the Brookfield RV-spindle set which is suitable for the viscosity range to be measured. For example, for a viscosity range between 200 and 800 mPa·s the spindle number 3 may be used, for a viscosity range between 400 and 1600 mPa·s the spindle number 4 may be used, and for a viscosity range between 800 and 3200 mPa·s the spindle number 5 may be used.

Solids Content

The solids content (also known as "dry weight") was determined using a Moisture Analyser HR73 from the company Mettler-Toledo, Switzerland, with the following settings: temperature of 120° C., automatic switch off 3, standard drying, 5 to 20 g of product.

Pigment Whiteness

Pigment whiteness R457 was measured using an ELREPHO 3000 from the company Datacolor according to ISO 2469:1994 (DIN 53145-2:2000 and DIN 53146:2000).

Light Scattering Coefficient

The light scattering coefficient "S" was measured by preparing a paper coating colour using 10 parts (on dry basis) of Acronal™ S 360 D, BASF, a paper coating binder, and 90 parts (on dry basis) of the calcium carbonate suspension and coated on a plastic support (Synteape, Argo Wiggins) at a range of different coat weight using a laboratory coater Typ Model 624 from Ericksen, 58675 Hemer, Germany. All coating colours had, if not reported otherwise, a solid content of 45.0 wt.-%.

The light scattering coefficient S is measured according to the method described in US 2004/0250970, wherein the ability to scatter light is expressed by the Kubelka-Munk light scattering coefficient, determined by the method, well-known to experts, described in the publications of Kubelka and Munk (Zeitschrift für Technische Physik 12, 539 (1931)), and of Kubelka (J. Optical Soc. Am. 38 (5), 448 (1948) and J. Optical Soc. Am. 44 (4), 330 (1954)) and U.S. Pat. No. 5,558,850. The light scattering coefficient S is quoted as the value interpolated at 20 $g/m^2$.

2. Examples

The following starting materials have been used for the examples:

TABLE 1

Starting materials.

| Compound | Chemical description |
|---|---|
| Dispersing agent 1 | Polyacrylate dispersant 70 mol-% sodium-30 mol-% calcium neutralized, Mw 5500; aqueous solution at 38 wt.-%; pH 8 |
| Dispersing agent 2 | 100 % sodium-neutralized polyacrylate, Mw = 3500 g/mol, pH = 8 |

Preparation of Aqueous Suspension 1 (AS1)

Norwegian marble (40-48 μm) was ground at a solid content of 25 wt.-% in a Dynomill Multilab from W. Bachofen AG (total volume of the grinding chamber=600 cm$^3$, mill speed=2 500 rpm, flow=500 cm$^3$/min, filled with 1070 g of melt fused grinding beads consisting of 68 wt.-% baddeleyite and 32 wt.-% amorphous silica, based on the total weight of grinding beads with a diameter in the range from 1.0 to 1.6 mm) until the $d_{50}$ was 8 μm. The suspension was centrifuged to obtain a cake with 75% solid content and a supernatant with 2% solid content. The cake was dispersed with dispersing agent 1 or 2 in an amount as given in Table 2 below at a solid content of 75 wt.-%.

Preparation of Aqueous Suspension 2 (AS2)

The supernatant from AS1 was placed in a settling jar and left for various days until the sediment had reached a solid content of 37%. The supernatant water was decanted and the sediment used as AS2.

Preparation and Grinding of the Mixture

AS1 was mixed with AS2, and or water. Additionally, the dispersant in an amount as given in Table 2 below was added. The mixture was vigorously stirred and pumped through the mill. One batch contained around 5 kg (dry) calcium carbonate. Subsequently, the obtained calcium carbonate containing suspension was ground at room temperature until the calcium carbonate containing material had the desired weight median particle size $d_{50}$, i.e. for about 60 minutes. For grinding a Dynomill Multilab from W. Bachofen AG (total volume of the grinding chamber=600 cm$^3$, mill speed=2 500 rpm, flow=500 cm$^3$/min, filled with 1 070 g of melt fused grinding beads consisting of 68 wt.-% baddeleyite and 32 wt.-% amorphous silica, based on the total weight of grinding beads with a diameter in the range from 1.0 to 1.6 mm) was used. Physical data of the obtained products are given in Table 2 below. It is to be noted that the ΔSSA refers to the difference of BET specific surface area of the inventive example compared to the corresponding comparative example.

TABLE 2

| | E1 | | E2 | | E3 | | E4 | | CE1 | | CE2 | | CE3 | | CE4 | |
|---|---|---|---|---|---|---|---|---|---|---|---|---|---|---|---|---|
| | AS1 | AS2 | AS1 | AS2 | AS1 | AS2 | AS1 | AS2 | AS1 | H$_2$O | AS1 | H$_2$O | AS1 | H$_2$O | AS1 | H$_2$O |
| sc [wt.-%] | 75 | 37 | 75 | 37 | 75 | 37 | 75 | 37 | 75 | — | 75 | — | 75 | — | 75 | — |
| PSD | | | | | | | | | | | | | | | | |
| <2 μm [wt.-%] | 20 | 64 | 20 | 64 | 20 | 64 | 20 | 64 | 20 | — | 20 | — | 20 | — | 20 | — |
| <1 μm [wt.-%] | 11 | 32 | 11 | 32 | 11 | 32 | 11 | 32 | 11 | — | 11 | — | 11 | — | 11 | — |
| Mixing ratio of AS1 and AS2 [dry/dry wt.-%] | 70 | 30 | 70 | 30 | 70 | 30 | 70 | 30 | 100 | — | 100 | — | 100 | — | 100 | — |
| DA1 to AS1 [ppm] | 600 | | 600 | | 600 | | 600 | | 600 | | 600 | | 600 | | 600 | |
| DA1 to Mixture [ppm] | 1 200 | | — | | 1 500 | | — | | 1 450 | | — | | 1 750 | | — | |
| DA2 to Mixture [ppm] | — | | 1 150 | | — | | 1 500 | | — | | 1 400 | | — | | 1 700 | |
| Sum DA | 1 800 | | 1 750 | | 2 100 | | 2 100 | | 2 050 | | 1 400 | | 2 350 | | 1 700 | |
| Time in the mill [min] | 45 | | 45 | | 56 | | 56 | | 60 | | 60 | | 75 | | 75 | |
| Mixture | | | | | | | | | | | | | | | | |
| sc [wt.-%] | 58.6 | | 57.8 | | 57.8 | | 58.1 | | 59.5 | | 59.8 | | 60.6 | | 60.9 | |
| BV [mPas] | 150 | | 140 | | 135 | | 155 | | 260 | | 110 | | 100 | | 180 | |
| pH | 9.5 | | 9.6 | | 9.5 | | 9.6 | | 9.4 | | 9.8 | | 9.6 | | 9.8 | |
| PSD | | | | | | | | | | | | | | | | |
| <2 μm [wt.-%] | 79 | | 78 | | 86 | | 87 | | 79 | | 78 | | 84 | | 87 | |
| <1 μm [wt.-%] | 45 | | 43 | | 51 | | 52 | | 43 | | 44 | | 50 | | 53 | |
| $d_{50}$ [μm] | 1.1 | | 1.2 | | 1.0 | | 1.0 | | 1.2 | | 1.2 | | 1.0 | | 0.9 | |
| $d_{98}$ [μm] | 4 | | 4 | | 3 | | 3 | | 4 | | 4 | | 4 | | 3 | |
| R457 [%] | 95.6 | | 95.4 | | 95.7 | | 95.6 | | 96.0 | | 96.3 | | 95.7 | | 96.3 | |
| Scat. [m$^2$/kg] | 129 | | 127 | | 135 | | 143 | | 135 | | 131 | | 134 | | 134 | |
| SSA [m$^2$/g] | 8.3 | | 8.0 | | 9.4 | | 9.2 | | 8.6 | | 8.6 | | 9.8 | | 10.1 | |
| ΔSSA [m$^2$/g] | −0.3 | | −0.6 | | −0.4 | | −0.8 | | — | | — | | — | | — | |

AS = aqueous suspension, DA = Dispersing agent, sc = solid content, BV = Brookfield Viscosity, scat. = Scattering, SSA = specific surface area (BET).

The comparison of E1 with CE1, E2 with CE2, E3 with CE3 and E4 with CE4 in Table 2 shows that the inventive process allows to manufacture a calcium carbonate-comprising material having a lower BET specific surface area. Thus, the inventive process for the manufacturing of a calcium carbonate-comprising material also results in a material allowing a lower consumption of dispersing agents in combination with improved optical properties as well as coating hold out. Furthermore, a grinding process according to the present invention is more time efficient and therefore also expected to be more energy efficient.

The invention claimed is:

1. A process for manufacturing a calcium carbonate-comprising material, the process comprising the steps of:
   a) providing at least two aqueous suspensions comprising a calcium carbonate-comprising material, wherein
      i) the first aqueous suspension has a solid content from 1.0 to 82.0 wt.-%, based on the total weight of the aqueous suspension, and a content of particles having a particle size <2 µm in the range from 1.0 to 30.0 wt.-%; and
      ii) the second aqueous suspension has a solid content from 10.0 to 82.0 wt.-%, based on the total weight of the aqueous suspension, and a content of particles having a particle size <2 µm in the range from >30.0 to 100.0 wt.-%;
   b) mixing the at least two aqueous suspensions provided in step a) to obtain an aqueous suspension mixture;
   c) grinding the aqueous suspension mixture obtained in mixing step b).

2. The process according to claim 1, wherein at least one dispersing agent is added to at least one of the at least two aqueous suspensions provided in step a) and/or to the aqueous suspension mixture obtained in mixing step b).

3. The process according to claim 2, wherein the at least one dispersing agent is selected from the group consisting of sodium, potassium, calcium, magnesium, lithium, strontium, primary amine, secondary amine, tertiary amine, and/or ammonium salts, whereby the amine salts are linear or cyclic, of at least partly neutralized homopolymers or copolymers of (meth)acrylic acid, maleic acid, fumaric acid, itaconic acid and derivatives of these acids, esters or amides, methylmethacrylate, methylacrylate, acrylamide, sodium hydrogen phosphate, polyphosphates, alkalipolyphosphates, carboxymethylcellulose, steric dispersants, comb polymers, and any mixture thereof.

4. The process according to claim 2, wherein the at least one dispersing agent is sodium polyacrylate having a molecular weight $M_w$ of from 4,000 to 10,000 g/mol.

5. The process according to claim 2, wherein the at least one dispersing agent is sodium polyacrylate having a molecular weight $M_w$ of from 4,000 to 8,000 g/mol.

6. The process according to claim 1, wherein the BET specific surface area of
   i) the calcium carbonate-comprising material in the aqueous suspension mixture obtained in grinding step c) has a BET specific surface area of between 0.1 and 30.0 $m^2/g$, as measured using nitrogen and the BET method according to ISO 9277, or
   ii) the calcium carbonate-comprising material in the aqueous suspension mixture obtained in grinding step c) has a BET specific surface area between 0.1 and 2.0 $m^2/g$ lower than the BET specific surface area of a calcium carbonate-comprising material manufactured by a process using water instead of the second aqueous suspension.

7. The process according to claim 1, wherein the BET specific surface area of
   i) the calcium carbonate-comprising material in the aqueous suspension mixture obtained in grinding step c) has a BET specific surface area of between 1.0 and 20.0 $m^2/g$, as measured using nitrogen and the BET method according to ISO 9277, or
   ii) the calcium carbonate-comprising material in the aqueous suspension mixture obtained in grinding step c) has a BET specific surface area between 0.1 and 1.5 $m^2/g$ lower than the BET specific surface area of a calcium carbonate-comprising material manufactured by a process using water instead of the second aqueous suspension.

8. The process according to claim 1, wherein the BET specific surface area of
   i) the calcium carbonate-comprising material in the aqueous suspension mixture obtained in grinding step c) has a BET specific surface area of between 2.0 and 14.0 $m^2/g$, as measured using nitrogen and the BET method according to ISO 9277, or
   ii) the calcium carbonate-comprising material in the aqueous suspension mixture obtained in grinding step c) has a BET specific surface area between 0.2 and 1.0 $m^2/g$ lower than the BET specific surface area of a calcium carbonate-comprising material manufactured by a process using water instead of the second aqueous suspension.

9. The process according to claim 1, wherein the BET specific surface area of
   i) calcium carbonate-comprising material in the aqueous suspension mixture obtained in grinding step c) has a BET specific surface area of between 8.0 and 10.0 $m^2/g$, as measured using nitrogen and the BET method according to ISO 9277, and
   ii) the calcium carbonate-comprising material in the aqueous suspension mixture obtained in grinding step c) has a BET specific surface area between 0.2 and 1.0 $m^2/g$ lower than the BET specific surface area of a calcium carbonate-comprising material manufactured by a process using water instead of the second aqueous suspension.

10. The process according to claim 1, wherein the aqueous suspension mixture obtained in grinding step c) has a Brookfield viscosity of between 50 and 5,000 mPa·s.

11. The process according to claim 1, the aqueous suspension mixture obtained in grinding step c) has a Brookfield viscosity of between 75 and 1,500 mPa·s.

12. The process according to claim 1, wherein the aqueous suspension mixture obtained in grinding step c) has a Brookfield viscosity of between 150 and 500 mPa·s.

13. The process according to claim 1, wherein the calcium carbonate-comprising material in the aqueous suspension mixture obtained in grinding step c) has a
   i) top cut particle size $d_{98}$ of ≤50.0 µm, and/or
   ii) weight median particle size $d_{50}$ between 0.1 and 10.0 µm.

14. The process according to claim 1, wherein the calcium carbonate-comprising material in the aqueous suspension mixture obtained in grinding step c) has a
   i) top cut particle size $d_{98}$ of ≤20.0 µm, and/or
   ii) weight median particle size $d_{50}$ between 0.5 and 5.0 µm.

15. The process according to claim 1, wherein the calcium carbonate-comprising material in the aqueous suspension mixture obtained in grinding step c) has a
   i) top cut particle size $d_{98}$ of ≤10.0 µm, and/or ii) weight median particle size $d_{50}$ between 1.0 and 2.0 µm.

16. The process according to claim 1, wherein the solid content
    i) of the first aqueous suspension is from 30.0 to 78.0 wt.-%, based on the total weight of the aqueous suspension, and/or
    ii) of the second aqueous suspension is from 30.0 to 40.0 wt.-%, based on the total weight of the aqueous suspension, and/or
    iii) of the aqueous suspension mixture obtained in grinding step c) is from 20.0 to 80.0 wt.-%, based on the total weight of the aqueous suspension.

17. The process according to claim 1, wherein the solid content
    i) of the first aqueous suspension is from 50.0 to 76.0 wt.-%, based on the total weight of the aqueous suspension, and/or
    ii) of the second aqueous suspension is from 34.0 to 43.0 wt.-%, based on the total weight of the aqueous suspension, and/or
    iii) of the aqueous suspension mixture obtained in grinding step c) is from 50.0 to 62.0 wt.-%, based on the total weight of the aqueous suspension.

18. The process according to claim 1, wherein at least one of the at least two aqueous suspensions provided in step a) is subjected to a concentration step, mechanical dewatering by means of settling, or forced settling by a centrifuge.

19. The process according to claim 1, wherein the calcium carbonate-comprising material is selected from group consisting of natural calcium carbonate, precipitated calcium carbonate, dolomite, and any mixture thereof.

20. The process according to claim 1, wherein the calcium carbonate-comprising material is natural calcium carbonate from marble, chalk and/or limestone.

21. The process according to claim 1, wherein the at least two aqueous suspensions provided in step a) comprise the first and the second aqueous suspension in an amount of more than 10.0 wt.-%.

22. The process according to claim 1, wherein the at least two aqueous suspensions provided in step a) comprise the first and the second aqueous suspension in an amount of more than 30.0 wt.-%.

23. The process according to claim 1, wherein the at least two aqueous suspensions provided in step a) comprise the first and the second aqueous suspension in an amount of more than 60.0 wt.-%.

24. The process according to claim 1, wherein the at least two aqueous suspensions provided in step a) comprise the first and the second aqueous suspension in an amount of more than 65.0 wt.-%.

25. The process according to claim 1, wherein the at least two aqueous suspensions provided in step a) consist of the first and the second aqueous suspension.

26. The process according to claim 1, further comprising the aqueous suspension mixture obtained in grinding step c) to remove at least a portion of water by mechanical means and/or thermal means.

27. The process according to claim 1, further comprising the steps of
    e) drying the aqueous suspension mixture obtained in grinding step c) or the aqueous suspension mixture obtained in concentrating step d) to remove at least a portion of water to obtain a partially dewatered calcium carbonate-comprising material or to obtain a dried calcium carbonate-comprising material; and optionally
    f) treating the dried calcium carbonate-comprising material obtained after step e) with at least one dispersing agent and re-diluting it to obtain an aqueous suspension comprising a dispersed calcium carbonate-comprising material, and/or
    g) treating the dried calcium carbonate-comprising material obtained after step e) with at least one saturated aliphatic linear or branched carboxylic acid and/or with at least one mono-substituted succinic anhydride and/or at least one mono-substituted succinic acid and/or salty reaction product(s) and/or with at least one phosphoric acid ester blend of one or more phosphoric acid mono-ester and/or reaction products thereof and one or more phosphoric acid di-ester and/or reaction products thereof to obtain a hydrophobized calcium carbonate-comprising material.

* * * * *